United States Patent [19]

Neumeier et al.

[11] 4,185,630
[45] Jan. 29, 1980

[54] COLOSTOMY APPARATUS

[75] Inventors: Erich Neumeier; Douglas J. Marver, both of Mosinee, Wis.

[73] Assignee: Diamond Shamrock Corporation, Dallas, Tex.

[21] Appl. No.: 824,808

[22] Filed: Aug. 15, 1977

[51] Int. Cl.² ............................................. A61F 5/44
[52] U.S. Cl. ..................................... 128/283; 128/272
[58] Field of Search ................... 128/283, 272, 272.1, 128/272.3

[56] References Cited

U.S. PATENT DOCUMENTS

| | | | |
|---|---|---|---|
| 2,397,051 | 3/1946 | Scherer | 128/272 |
| 3,055,368 | 9/1962 | Baxter | 128/283 |
| 3,463,357 | 8/1969 | McLean | 128/272 |

Primary Examiner—Robert W. Michell
Assistant Examiner—Milford A. Juten
Attorney, Agent, or Firm—Stuart L. Melton

[57] ABSTRACT

Ostomy collection pouch appliances suitable for operation in a first, non-vented, or second, vented but substantially leak-proof, mode and provided with a sealed port member including a heat seal configuration which provides the user with directional information concerning proper opening of the port.

8 Claims, 4 Drawing Figures

U.S. Patent
Jan. 29, 1980
4,185,630
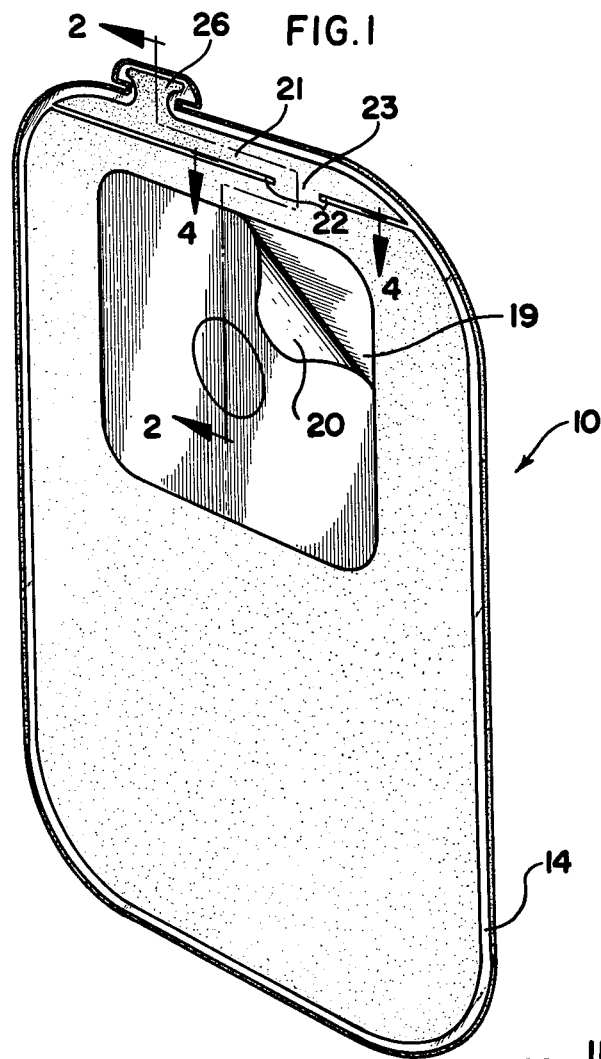
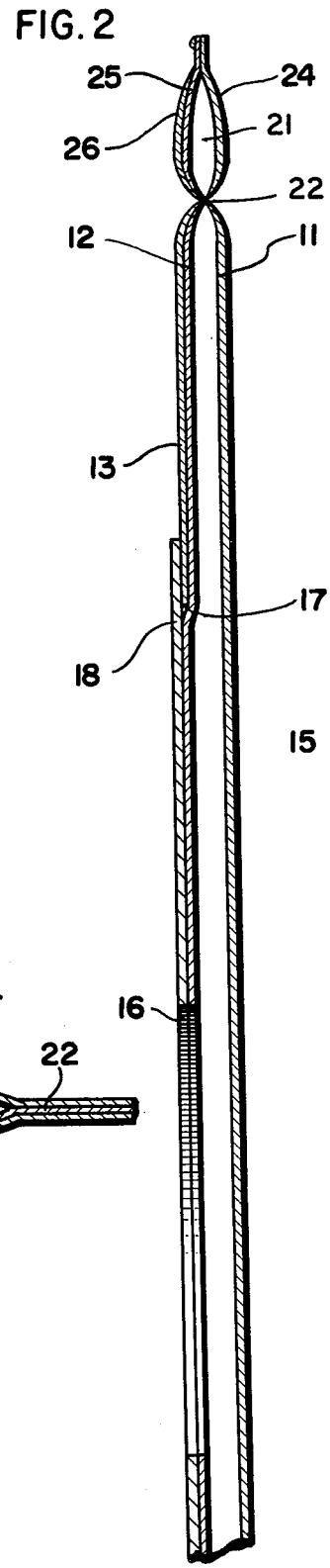
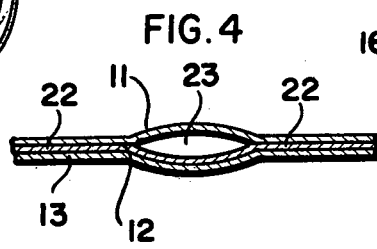
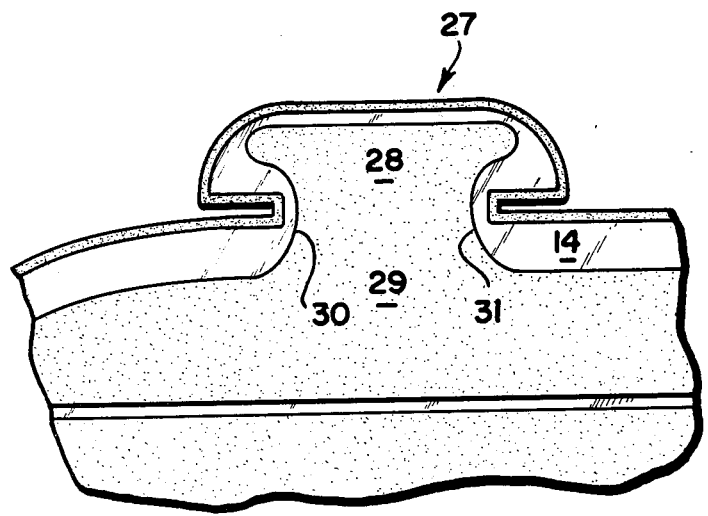

COLOSTOMY APPARATUS

BACKGROUND

The present invention relates generally to drainage pouches for use in collection of waste materials at the site of a colostomy or ileostomy and more specifically concerns a pouch susceptible to operation in either a vented or non-vented mode.

The natural accumulation of gases from the digestive system of an ostomy patient has provided a problem of long standing in the manufacture of waste collection pouches. This is so because an ostomy pouch is ideally tightly sealed at and around the stoma site and desirably the pouch and seal are impervious to gases and liquids. Gases from the digestive system thus have a tendency to accumulate and "balloon" the gas-tight collection pouch and the ostomate frequently must initiate a small puncture in the pouch to release the gas. With a puncture of the pouch at almost any location, there exists a great likelihood of leakage of liquid wastes onto the outer garments of the ostomate.

Among the solutions proposed for venting of accumulating gases are providing pouches with a performed hole which is theoretically capable of being opened and re-sealed and providing a perforated tear-away corner on the pouch.

Providing re-closable holes and tear-away corners require costly manufacturing processes and have not adequately solved the problem. Leakage still occurs at re-closable holes due to their proximity to liquid wastes. Perforations necessary to develop tear-away corners will either be too shallow to make precise opening easy or will be too deep and destroy the vapor-tightness of the pouches, rendering them essentially permanently vented with no safeguards against liquid leakage.

Another prior art proposal relates to providing a permanent passage for gas escape which is an integral part of the pouch itself but which minimizes the likelihood that liquid waste material will also escape from the pouch. U.S. Pat. No. 3,055,368 discloses a permanently vented collection pouch of thermoplastic material provided with selectively placed heat seals which form a permanent, transversely-extending gas escape channel a the top of the pouch with laterally spaced-apart passages for open communication between the inside and outside of the pouch. While the leak-proof, continuously-venting pouches of the U.S. Pat. No. 3,055,368 involve no expensive extra manufacturing steps and are adequate for the needs of those patients for whom gas discharge is a chronic, recurrent problem, their use has not been widespread owing to the fact that continuous, unpredictable and involuntary venting through permanent gas escape passages and channels is frequently the cause of embarrassment for ostomates. It is generally the ostomate's desire that the pouch be initially of a non-vented variety which could be vented quickly and in private if and when excessive gas build-up occurs.

Because gas accumulation is not a problem for all ostomates and tends to vary in severity from day to day for any individual patient, providing permanently vented pouches for a segment of the ostomate population requires stocking of multiple types of pouches by the ostomate and by the pharmacist, hospital, or other supply source. The logistics of large scale stocking of vented and non-vented varieties of pouches by suppliers is compounded by the fact that pouches are already ordinarily stocked in multiple types according to stoma opening size.

Recent developments in ostomy pouch design of interest to the present invention include those of U.S. Pat. No. 3,931,819, whereby comfort to the skin of an ostomate is materially enhanced by providing a soft layer of thermoplastic material along the back of the pouch and heat-sealing the former about its entire periphery to the pouch itself. While the soft, insulating layer is ordinarily opaque, the heat seals or welds are not and they provide a transparent or at least translucent edge or rim about the entire perhiphery of the devices.

SUMMARY

The present invention provides drainage pouches for use by ostomy patients which incorporate advantages of prior art devices having soft backing layers and relatively leakproof gas venting passages, but which are capable of selective conversion from non-venting to venting according to the specific needs of the ostomate. According to one aspect of the invention a peripheral transparent or translucent heat seal about a port member projecting from the upper portion of the pouch has a shape which provides the user with directional information for conversion of a pouch from an initial non-vented mode of use to a subsequent permanently-vented but leakproof mode of use.

The pouches of the invention are readily and inexpensively manufactured with a minimum of extra process steps and require no adhesive patches or other additional parts. Due to their easy conversion from non-vented to vented modes of use according to the needs and desires of the patient, multipurpose pouches of the invention reduce inventory problems for ostomates and suppliers of pouches and lessen the overall cost of pouches to the consumer by keeping manufacturers' product lines to a minumum number without a concurrent elimination of choices to the customers.

Further aspects and advantages of the invention will become apparent to those skilled in the art upon consideration of the following detailed description of a preferred embodiment in conjunction with reference to the accompanying drawings, wherein:

FIG. 1 is a perspective view of the rear portion of a pouch of the invention;

FIG. 2 is an enlarged fragmentary cross-sectional view along lines 2—2 of FIG. 1;

FIG. 3 is a detailed enlarged view of a sealed gas-venting port member of a pouch of the invention; and FIG. 4 is an enlarged fragmentary sectional view taken along lines 4—4 of FIG. 1.

DETAILED DESCRIPTION

FIGS. 1 and 2 illustrate a disposable pouch 10 consisting of a front wall 11 and back wall 12 formed from pliable, moisture-impermeable thermoplastic sheet material. Substantially coextensive with the entire back wall 12 is a soft layer 13 of thermoplastic, preferably moisture-absorbent, material. Walls 11 and 12 and layer 13 are preferably die-cut to the same dimensions and are heat-sealed together at their peripheries by a continuous peripheral weld 14 to provide an enclosed interior pouch space 15 between walls 11 and 12 for collection of waste.

Access to enclosed space 15 is provided through circular stoma opening 16 in back wall 12. Soft layer 13 also has a circular opening 17 which is preferably of somewhat larger circumference than opening 16 to allow for attachment about opening 15 of back wall 12 of a generally annular patch 18. Patch 18 assists in mounting of pouch 10 upon the abdomen of the patient and is preferably previded with an adhesive layer 19 on its outer (patient-facing) surface. Adhesive layer 19 is ordinarily covered and protected prior to use by a suitable plasticized release paper 20.

In the course of pouch fabrication, and preferably during formation of the continuous peripheral weld 14, a gas channel 21 is developed across the top of pouch 10 and between walls 11 and 12 by applying a horizontally-extending, discontinuous weld 22 which effectively seals the top of space 15 except for open, unwelded portion 23 which functions as a passage through which gas in the pouch may enter channel 21.

Each of walls 11 and 12 and layer 13 has an outwardly- (and operatively upwardly-) extending tab, 24, 25, and 26 respectively. During formation of continuous weld 14, tabs 24, 25 and 26 are superposed and sealed together to form gas port member 27 in a configuration providing a relatively widened, easily grippable, head portion 28 and relatively narrowed neck portion 29 (FIG. 3). The interior of port member 27 between wall tabs 23 and 24 is continuous with and open to channel 21, but otherwise entirely sealed from the outside. When an opaque soft layer 13 is employed, forming weld 14 will render the heat-sealed portions of the soft layer transparent or at least translucent and provide a continuous outline or frame of head and neck portions of port member 27. Opposing linear segments 30, 31 of the weld outline signify to the user the precise location at which a cut or tear may be initiated to rupture weld 14 and permit venting of gas.

In use, the ostomy patient will adhesively apply pouch 10 to the stoma site. Upon the occurence of substantial discharge of gas into space 15, port member 27 may be opened by transversely cutting the material at narrowed neck 29 along the directional lines indicated by the opposed linear segments 30, 31 of transparent or translucent weld 14. Upon rupture of weld 14 and/or removal of the head portion of port 26, a permanent, continuous passage is provided for gas travelling upwardly from pouch interior 15, through passage 23, laterally along the transverse channel 21 and outwardly through the opening provided upon rupture of continuous weld 14 at neck 29 of port member 27. Clearly, it is preferable that passage 23, formed by discontinuous weld 22, be located at a site substantially laterally spaced-away from neck 29 of port member 27 to maximize the length of channel 21 and consequently minimize the likelihood of escape of liquid wastes from pouch interior 15.

From the foregoing detailed description of a preferred embodiment, it will be seen that pouches constructed according to the present invention are easily fabricated from available thermoplastic materials without excess manufacturing steps and are equally suited to use by all ostomates, whether gas build-up is a chronic and recurrent or merely occasional problem. It is expected, for example, that an ostomate for whom gas collection is only an infrequent problem will nonetheless obtain substantial benefit from use of a pouch of the invention owing to its easy conversion from non-vented to vented modes of operation by severing of port member neck 29 along a line joining curves 30, 31 of weld 14. As is the case with pouches having preformed holes for venting of collected gas, the ostomate may optionally attempt to re-seal the pouch by placing n adhesive tape or patch at the site of the removal of port head portion. Such practice is expected to be more successful than the re-sealing of holes pre-cut in other portions of the pouch because the opening is "protected" from leakage by the convoluted passageway system involving passage 23 and channel 21.

Numerous modifications and variations of the above-disclosed invention are expected to occur to those skilled in the art upon consideration of the foregoing disclosure and therefore only such limitations as appear in the appended claims should be placed thereon.

We claim:

1. In an ostomy collection pouch comprised of front and back sheets of thermoplastic material sealed at their periphery to form said pouch, a relatively soft layer of thermoplastic material integrally sealed to at least a portion of said back sheet of said pouch, said back sheet and soft layer having a stoma-accommodating opening therein and said pouch including a transversely extending gas escape channel in communication with the pouch interior at its upper portion, the improvement comprising:

outwardly extending superposed tabs on said sheets disposed at the upper portion of said pouch;
   a gas escape port member, the interior of which is in communication with said gas escape channel and formed by a seal at the edges of said outwardly extending superposed tabs,
   said port member consisting of a relatively broad head portion and a relatively narrower neck portion joining said port member to said pouch and said gas escape channel and framed by said edge seal, said edge seal having opposing, inwardly extending linear means for signifying a site for initiation of an opening in said port member,
   whereby said pouch is initially operative in a first, sealed, non-gas-venting mode and convertible to operation in a second gas-venting but substantially leakproof mode by initiation of said opening to rupture said edge seal.

2. The pouch of claim 1 wherein said soft layer of thermoplastic is comprised of a moisture-absorbent material.

3. The pouch of claim 1 wherein said stoma-accommodating opening in said soft layer is of greater dimension than said stoma-accommodating opening in said back sheet.

4. The pouch of claim 3 further comprising annular adhesive mounting means secured to said stoma-accommodating opening of said back sheet for mounting said pouch in an operative, discharge-receiving position.

5. The pouch of claim 1 wherein said seal at the periphery of said front and back sheets is a heat seal.

6. The pouch of claim 1 wherein said relatively broad head portion and relatively narrower neck portion are opaque and said edge seal comprises a translucent weld whereby said head and neck portions are framed by said weld.

7. The pouch of claim 1 wherein said pouch is converted from said first, sealed, non-gas-venting mode to said second gas-venting mode by rupturing said edge seal transversely at said neck portion to remove the head portion of said port member.

8. The pouch of claim 1 wherein said outwardly extending superposed tabs on said sheets are further comprised of said soft layer.